United States Patent [19]

White et al.

[11] 4,235,910
[45] Nov. 25, 1980

[54] BENZOQUINOLIZINES HAVING BLOOD PRESSURE LOWERING ACTIVITY, AND IN SOME INSTANCES, ANTI-SECRETORY ACTIVITY

[75] Inventors: John F. White, Wokingham; Terence J. Ward, Slough, both of England

[73] Assignee: John Wyeth & Brother Limited, Taplow, England

[21] Appl. No.: 38,029

[22] Filed: May 10, 1979

[30] Foreign Application Priority Data

May 26, 1978 [GB] United Kingdom ............... 23327/78

[51] Int. Cl.³ ..................... A61K 31/47; C07D 455/06
[52] U.S. Cl. ........................................ 424/258; 546/95
[58] Field of Search ........................... 546/95; 424/258

[56] References Cited

U.S. PATENT DOCUMENTS

| 3,634,431 | 1/1972 | Van Dyke, Jr. ................. 424/258 X |
| 3,635,986 | 1/1972 | Van Dyke, Jr. ........................ 546/95 |
| 4,076,820 | 2/1978 | Archibald, et al. .................. 424/258 |

OTHER PUBLICATIONS

Van Dyke, et al., J. Med. Chem. vol. 15, pp. 91-94 (1972).
Kawanishi, Chemical & Pharmaceutical Bulletin (Japan) vol. 10, No. 3, pp. 185-190 (1962).
Gerszberg, et al., Anales Asoc. Quim. Argentina, vol. 60, pp. 331-346 (1972).

Primary Examiner—Donald G. Daus
Assistant Examiner—Diana G. Rivers
Attorney, Agent, or Firm—Arthur E. Wilfond

[57] ABSTRACT

The invention concerns benzoquinolizines of the general formula (I)

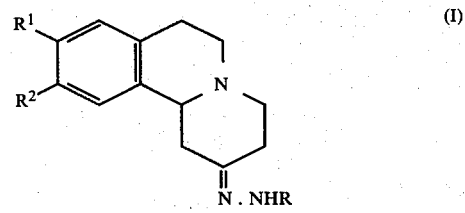

and the pharmaceutically acceptable acid addition salts thereof, wherein $R^1$ and $R^2$ which may be the same or different, each represent hydrogen, lower alkyl, lower alkoxy or halogen and R represents —$CXNHR^3$ (where X is O, S or =NH and $R^3$ is hydrogen or lower alkyl) or —$(CH_2)_nR^4$ (where n is 0 or 1 and $R^4$ is aryl). These compounds lower blood pressure. Some are also anti-ulcer agents. The compounds in which $R^1$, $R^2$ and R are as defined above, with the proviso that when R is phenyl, $R^1$ and $R^2$ are not both lower alkoxy, are novel.

12 Claims, No Drawings

BENZOQUINOLIZINES HAVING BLOOD PRESSURE LOWERING ACTIVITY, AND IN SOME INSTANCES, ANTI-SECRETORY ACTIVITY

This invention relates to benzoquinolizines, in particular to pharmaceutical compositions containing benzoquinolizines and the use of these benzoquinolizines and to certain novel benzoquinolizines and to processes for preparing them.

Thus in one aspect the present invention provides novel benzoquinolizines of the general formula (I)

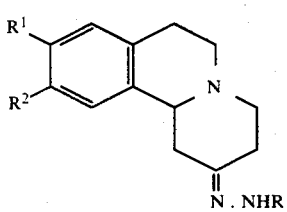

and the pharmaceutically acceptable acid addition salts thereof, wherein $R^1$ and $R^2$ which may be the same or different, each represent hydrogen, lower alkyl, lower alkoxy or halogen and R represents —$CXNHR^3$ (where X is O, S or =NH and $R^3$ is hydrogen or lower alkyl) or —$(CH_2)_nR^4$ (where n is 0 or 1 and $R^4$ is aryl) with the proviso that when R is phenyl $R^1$ and $R^2$ are not both lower alkoxy.

The term "lower" as used herein means that the radical referred to contains 1 to 6 carbon atoms. Preferably the radical contains 1 to 4 carbon atoms.

The aryl radical $R^4$ is preferably a phenyl group or a substituted phenyl group. The phenyl group may be substituted by one or more substituents chosen from, for example, halogen (e.g. fluorine, chlorine or bromine), lower alkyl (e.g. methyl, ethyl, propyl, butyl), lower alkoxy (e.g. methoxy, ethoxy, propoxy), alkylenedioxy (e.g. methylenedioxy or ethylenedioxy), amino, lower alkylamino, diloweralkylamino or trifluoromethyl.

n is preferably 0

$R^3$ is preferably hydrogen but it can also be lower alkyl (e.g. methyl, ethyl, propyl or butyl).

Examples of $R^1$ and $R^2$ are hydrogen, lower alkyl (such as methyl, ethyl, propyl or butyl), lower alkoxy (such as methoxy, ethoxy, propoxy or butoxy) or halogen (such as fluorine, chlorine or bromine). $R^1$ and $R^2$ can be different or the same. They are preferably both hydrogen.

The preferred compounds of general formula (I) are those wherein R is —$(CH_2)_nR^4$. These compounds are hydrazones, e.g. phenylhydrazones. The compounds in which R is —$CONHR^3$ are semicarbazones, those in which R is —$CSNHR^3$ are thiosemicarbazones and those in which R is C(=NH)$NHR^3$ are amidinonohydrazones.

The compounds of the invention can be prepared by known processes for preparing hydrazones, semicarbazones, thiosemicarbazones or amidinonohydrazones. For example a ketone of general formula (II)

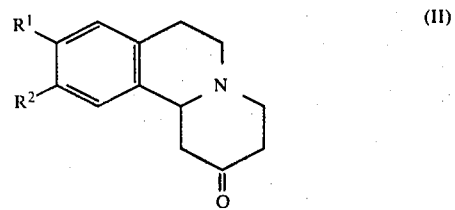

(wherein $R^1$ and $R^2$ are as defined above) can be reacted with a compound of general formula (III)

$$NH_2NHR \qquad (III)$$

(where R is as defined above) or a salt thereof. If desired, the reaction can be carried out in presence of a catalyst e.g. a basic catalyst such as pyridine. The reaction is preferably carried out in an inert organic solvent. If necessary a reactive substituent group may be protected during the reaction and the protecting group removed at a later stage. Once the compound of general formula (I) has been prepared, then, if necessary, a substituent in the molecule may be converted into another substituent specified in connection with general formula (I).

If in the process described above the compound of the invention is obtained as an acid addition salt, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The starting ketones of general formula (II) may be prepared by the procedures described, for example, in Beke et al, Chem. Ber., 1962, 95, 2132.

Since the compounds of the invention possess at least one asymmetric carbon atom, optical enantiomorphs are possible and the compounds of the invention may be in the form of pure enantiomorphs or mixtures of such enantiomorphs, such as racemates. If, for example, the starting ketone of general formula (II) is an optical enantiomorph the compound of the invention will be obtained in the form of an optical enantiomorph, while if the starting ketone is a racemate the compound of the invention will also be obtained in the form of a racemate. If required, a racemate may be resolved by methods known in the art.

The novel compounds of the invention and certain related compounds possess pharmacological activity. Thus compounds of general formula (I) wherein $R^1$ and $R^2$ which may be the same or different, each represent hydrogen, lower alkyl, lower alkoxy or halogen and R represents —$CXNHR^3$ (where X is O, S or =NH and $R^3$ is hydrogen or lower alkyl) or —$(CH_2)_nR^4$ (where n is 0 or 1 and $R^4$ is aryl), and their pharmaceutically acceptable acid addition salts lower blood pressure as indicated by standard hypotensive or antihypertensive pharmacological procedures. For example, 1,3,4,6,7,11bα-hexahydro-2H-benzo[a]quinoliz-2-one phenylhydrazone, a representative compound of the invention, shows antihypertensive activity at a dose of 50 mg/kg when administered to hypertensive rats.

Some of the compounds are also anti-ulcer agents which possess anti-secretory activity in the test of H. Shay, D. Sun and H. Greenstein, Gastroenterology, 1954, 26, 903-13. Compounds which possess anti-secretory activity are exemplified by 2-(1, 3, 4, 6, 7, 11bα-hexahydro-2H-benzo[a]-quinolizin-2-ylidene)-hydrazinecarbothioamide and 2-(1, 3, 4, 6, 7, 11bα-hexahydro-2H-benzo[a]quinolizin-2-ylidene)-hydrazinecarboxamide.

In one aspect the invention includes a pharmaceutical composition comprising a compound of general formula (I) wherein $R^1$ and $R^2$ which may be the same or different, each represent hydrogen, lower alkyl, lower alkoxy or halogen and R represents —CXNHR$^3$ (where X is O, S or =NH and $R^3$ is hydrogen or lower alkyl) or —(CH$_2$)$_n$R$^4$ (where n is 0 or 1 and $R^4$ is aryl or a pharmaceutically acceptable salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

The pharmaceutical compositions possessing antisecretory activity may be administered as anti-ulcer compositions. Those compositions may be administered orally in liquid or solid composition form and such compositions may include one or more antacid ingredients, e.g. aluminium hydroxide, magnesium hydroxide, bismuth carbonate, aluminium glycinate, calcium carbonate, magnesium trisilicate, sodium bicarbonate or the alumina gel described in U.K. Pat. Specification No. 1,284,394.

The following Examples illustrate the invention. Examples 1 to 6 illustrate the preparation of novel compounds while Example 7 illustrate the preparation of a known compound.

EXAMPLE 1

2-(1,3,4,6,7,11bα-Hexahydro-2H-benzo[a]quinolizin-2-ylidene) hydrazinecarbothioamide 1,3,4,6,7,11bα-Hexahydro-2H-benzo[a]quinolizin-2-one (1.0 g) was dissolved in absolute ethanol (12 cm$^3$) and pyridine (6 cm$^3$) and treated with thiosemicarbazide (0.47 g). The clear solution was heated to reflux for 1.5 hours and allowed to stand overnight. Ethanolic hydrogen chloride was then added until no further precipitation occurred (pH 7). The precipitated solid was collected by filtration and washed with cold ethanol. On further standing, a second crop was obtained.

The combined first and second crops were dissolved in a mimimum volume of hot water (5 cm$^3$) and diluted with ethanol (25 cm$^3$). The crystals which separated were collected after three days, washed well with ethanol, and dried to give the thiosemicarbazone title compound as the hydrochloride hydrate, (0.46 g.) pale yellow rods, m.p. 188°-190° C. (dec).

EXAMPLE 2

2-(1,3,4,6,7,11bα-Hexahydro-2H-benzo[a]quinolizin-2-ylidene)hydrazinecarboxamide 1,3,4,6,7,11bα-Hexahydro-2H-benzo[a]quinolizin-2-one (1.0 g.) was dissolved in absolute ethanol (12 cm$^3$) and pyridine (6 cm$^3$) and treated with semicarbazide hydrochloride (0.57 g). The turbid mixture was heated to reflux for 1.5 hours and allowed to stand overnight. The crude product was filtered off, and the sticky solid recrystallised from water and then from water/ethanol to give the semi-carbazone title compound as the hydrochloride (0.81 g.) colourless crystals, m.p. 226°-227° C. (dec).

EXAMPLE 3

1,3,4,6,7,11bα-Hexahydro-2H-benzo[a]quinolizin-2-one phenylhydrazone

A suspension of 1,3,4,6,7,11bα-hexahydro-2H-benzo[a]-quinolizin-2-one (0.2 g) and phenylhydrazine hydrochloride (0.15 g) in ethanol (20 cm³) was stirred and heated to reflux for 17 h. The mixture dissolved within 5 min and became turbid after a further 10 min. The mixture was reduced in volume in vacuo, treated with one drop of ethanolic hydrogen chloride and a little ethyl acetate and cooled. Filtration afforded the title phenylhydrazone, as the hydrochloride quarterhydrate (0.20 g), cream micro-needles, m.p. 205°–208° C. (dec).

EXAMPLE 4

2-(1,3,4,6,7,11bα-Hexahydro-9,10-dimethoxy-2H-benzo[a]quinolizin-2-ylidene)hydrazinecarboximidamide A mixture of sodium (0.22 g) and aminoguanidine sulphate (1.32 g) in ethanol (10 cm³) was stirred and heated to reflux for 1 h. It was then filtered into a 100 cm³ flask and washed in with more ethanol (3 cm³). A mixture of 1,3,4,6,7,11bα-hexahydro-9,10-dimethoxy-2H-benzo[a]quinolizin-2-one (1.26 g.) and dry pyridine (6 cm³) was added, and the mixture stirred and refluxed for 4 h. The solvent was evaporated and the residue dissolved as far as possible in ethanol (10 cm³). The turbid solution was acidified with ethanolic hydrogen chloride and allowed to cool. The precipitated cream crystals were filtered, washed well with ethanol and dried (1.37 g). This product was triturated with hot 75% aq. methanol, stirred to break up lumps, cooled and filtered to give the amidinohydrazine title compound as the dihydrochloride (1.01 g), colourless crystals, m.p. 243°–243.5° C. (dec).

EXAMPLE 5

1-(1,3,4,6,7,11bα-Hexahydro-2H-benzo[a]quinolizin-2-yl-idene)-4-methyl thiosemicarbazone A mixture of 1,3,4,6,7,11bα-hexahydro-2H-benzo[a]-quinolizin-2-one (2.65 g.) and 4-methylthiosemicarbazide (1.38 g) in ethanol (40 cm³) with acetic acid (5 drops) was heated to reflux for 4 h. The clear solution was then cooled in the refrigerator over the weekend, and the precipitated product filtered and washed with ice-cold ethanol to give 1-(1,3,4,6,7,11bα-hexahydro-2H-benzo[a]-quinolizidene-2-yl)-4-methyl thiosemicarbazone (3.46 g) as pale-yellow elongated hexagons, m.p. 188°–190° C. (dec).

The thiosemicarbazone (2.0 g) was dissolved in a hot mixture of ethanol (40 cm³) and methanol (40 cm³), acidified with ethanolic hydrogen chloride, and reduced in volume to about 20 cm³ by evaporation. The clear solution was cooled in the refrigerator overnight, stirred to break up lumps, and the solid filtered and washed with ethanol. The sticky product was dissolved in hot water (5 cm³), diluted with ethanol (30 cm³) and cooled in the refrigerator overnight. The feathery precipitate was filtered and washed with ethanol to give the hydrochloride of the title compound (0.70 g) as colourless crystals, m.p. 198°–200° C. (dec.).

EXAMPLE 6

1,3,4,6,7,11bα-Hexahydro-2H-benzo[a]quinolizin-2-one 4-chlorophenylhydrazone

A mixture of 1,3,4,6,7,11bα-hexahydro-2H-benzo[a]-quinolizin-2-one (1.13 g.) and 4-chlorophenylhydrazine, hydrochloride (1.00 g.) in ethanol (25 cm³) was stirred and heated to reflux for 4 h. The precipitate was filtered and washed well with ethanol. Further purification was effected by trituration with boiling methanol and re-filtering to give the title compound as the hydrochloride (1.00 g), cream crystals (which rapidly acquired a brownish tinge), m.p. 205°–208° C. (dec).

EXAMPLE 7

9,10-Dimethoxy-1,3,4,6,7,11bα-hexahydro-2H-benzo[a]quinolizin-2-one phenylhydrazone A mixture of 1,3,4,6,7,11bα-hexahydro-9,10-dimethoxy-2H-benzo[a]quinolizin-2-one (1.37 g) and phenylhydrazine, hydrochloride (0.76 g) was stirred and heated to reflux for 4 h. The precipitate was filtered and washed well with ethanol. Trituration with boiling methanol and refiltering gave the title compound as the hydrochloride crystals, m.p. 232°–3° C. (dec).

We claim:

1. A compound selected from the group consisting of a benzoquinolizine of the formula (I)

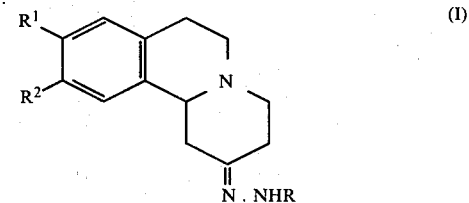

and a pharmaceutically acceptable acid addition salt thereof, wherein $R^1$ and $R^2$, which may be the same or different, each represent hydrogen, lower alkyl, lower alkoxy or halogen and R represents —CXNHR³ (where X is O, S or =NH and $R^3$ is hydrogen or lower alkyl) or —(CH₂)$_n$R⁴ (where n is 0 or 1 and $R^4$ is a phenyl group or a phenyl group substituted by one or more substituents selected from the group consisting of halogen, lower alkyl, lower alkoxy, alkylenedioxy, amino, lower alkylamino di-loweralkylamino and trifluoromethyl) with the proviso that when R is phenyl $R^1$ and $R^2$ are not both lower alkoxy.

2. A compound according to claim 1 wherein R represents —CXNHR³, where X and $R^3$ are as defined in claim 1.

3. A compound according to claim 1 wherein R represents —(CH₂)$_n$R⁴ where n and $R^4$ are as defined in claim 1.

4. A compound according to claim 1 which is 2-(1,3,4,6,7,11bα-hexahydro-2H-benzo[a]quinolizin-2-ylidene)hydrazinecarbothioamide or a pharmaceutically acceptable acid addition salt thereof.

5. A compound according to claim 1 which is 2-1,3,4,6,7,11bα-hexahydro-2H-benzo[a]quinolizin-2-ylidene)hydrazinecarboxamide or a pharmaceutically acceptable acid addition salt thereof.

6. A compound according to claim 1 which is 1,3,4,6,7,11bα-hexahydro-2H-benzo[a]quinolizin-2-one phenylhydrazone or a pharmaceutically acceptable acid addition salt thereof.

7. A compound according to claim 1 which is 2-(1,3,4,6,7,11bα-hexahydro-9,10-dimethoxy-2H-benzo[a]quinolizin-2-ylidene)hydrazinecarboximidamide or a pharmaceutically acceptable acid addition salt thereof.

8. A compound according to claim 1 which is 1-(1,3,4,6,7,11bα-hexahydro-2H-benzo[a]quinolizin-2-ylidene)-4-methyl thiosemicarbazone or a pharmaceutically acceptable acid addition salt thereof.

9. A compound according to claim 1 which is 1,3,4,6,7,11bα-hexahydro-2H-benzo[a]quinolizin-2-one 4-chlorophenylhydrazone or a pharmaceutically acceptable acid addition salt thereof.

10. A pharmaceutical composition having blood pressure lowering activity which comprises a compound selected from the group consisting of a benzoquinolinzine of the formula (I)

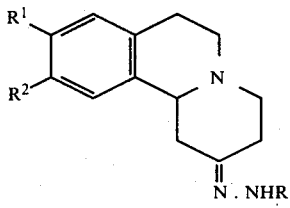

(I)

and a pharmaceutically acceptable acid addition salt thereof, wherein $R^1$ and $R^2$, which may be the same or different, each represent hydrogen, lower alkyl, lower alkoxy or halogen and R represents —$CXNHR^3$ (where X is O, X or =NH and $R^3$ is hydrogen or lower alkyl) or —$(CH_2)_nR^4$ (where n is 0 or 1 and $R^4$ is a phenyl group substituted by one or more substituents selected from the group consisting of halogen, lower alkyl, lower alkoxy, alkylenedioxy, amino, lower alkylamino, diloweralkylamino and trifluoromethyl) in association with a pharmaceutically acceptable carrier.

11. A method of lowering and blood pressure in a warm blooded mammal which comprises administering to said mammal a hypotensively or antihypertensively effective amount of a compound selected from the group consisting of a benzoquinolizine of the formula (I)

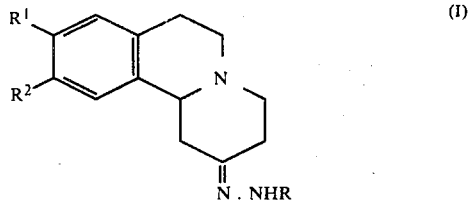

(I)

and a pharmaceutically acceptable acid addition salt thereof, where $R^1$ and $R^2$, which may be the same or different, each represent hydrogen, lower alkyl, lower alkoxy or halogen and R represents —$CXNHR^3$ (where X is O, X, or =NH and $R^3$ is hydrogen or lower alkyl) or —$(CH_2)_nR^4$, where n is 0 or 1 and $R^4$ is a phenyl group or a phenyl group substituted by one or more substituents selected from the group consisting of halogen, lower alkyl, lower alkoxy, alkylenedioxy, amino, lower alkylamino, di-loweralkylamino and trifluoromethyl.

12. A method of treating ulcers in a warm blooded mammal which comprises administering to said mammal an anti-secretory effective amount of a compound selected from the group consisting of 2-(1,3,4,6,7,11bα-hexahydro-2H-benzo[a]-quinolizin-2-ylidene)-hydrazinecarbothioamide and 2-(1,3,4,6,7,11bα-hexahydro-H-benzo[a]quinolizin-2-ylidene)-hydrazinecarboxamide and their pharmaceutically acceptable said addition salts.

* * * * *